Figure 1:
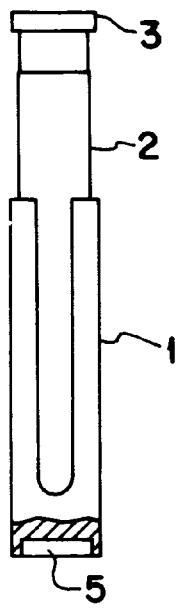

United States Patent

Riekkinen

Patent Number: 6,085,603
Date of Patent: *Jul. 11, 2000

[54] METHOD FOR MARKING OF A VESSEL AND A HANDLING DEVICE FOR APPLYING OF THE METHOD

[75] Inventor: Martti Riekkinen, Kuopio, Finland

[73] Assignee: Clids Oy, Kuopio, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/817,351

[22] PCT Filed: Sep. 15, 1994

[86] PCT No.: PCT/FI94/00406

§ 371 Date: Apr. 10, 1997

§ 102(e) Date: Apr. 10, 1997

[87] PCT Pub. No.: WO96/08433

PCT Pub. Date: Mar. 21, 1996

Related U.S. Application Data

[63] Continuation of application No. PCT/FI94/00406, Sep. 15, 1994.

[51] Int. Cl.$^7$ .................................................. G01N 1/00
[52] U.S. Cl. ............................................. 73/864.21
[58] Field of Search ........................ 73/864.21, 864.22; 422/63–67

[56] References Cited

U.S. PATENT DOCUMENTS

| | | |
|---|---|---|
| 3,526,125 | 9/1970 | Gilford et al. . |
| 3,660,638 | 5/1972 | Oberli . |
| 3,818,188 | 6/1974 | Hertel et al. . |
| 3,916,157 | 10/1975 | Roulette et al. . |
| 5,651,941 | 7/1997 | Stark et al. . |

FOREIGN PATENT DOCUMENTS

| | | |
|---|---|---|
| 039 145 | 11/1981 | European Pat. Off. . |
| 183 097 | 6/1986 | European Pat. Off. . |
| 243 915 | 11/1987 | European Pat. Off. . |
| 351 988 | 1/1990 | European Pat. Off. . |
| 494 066 | 7/1992 | European Pat. Off. . |
| 2 344 930 | 4/1974 | Germany . |
| 1 401 668 | 7/1975 | United Kingdom . |

Primary Examiner—Robert Raevis
Attorney, Agent, or Firm—Pillsbury Madison & Sutro LLP

[57] ABSTRACT

The object of the invention is a method for making a container for the identification of the samples whixh it contains, in which method the container is placed in a holder and the holder includes a memory unit into which the machine readable identification data for the identification of the container in the holder is stored. In addition, the object of the invention is an equipment for the application of the method. In order to improve the processing of the sample in the method according to the invention the identification data stored in the memory unit is read by the reading device of the handling equipment and by the instruments of the handling equipment the sample is processed in a predetermined way and the data concerning the processing is transfered into the memory unit. The handling equipment relating to the invention consists of a reading device for reading the identification data and the instruments for processing the sample.

3 Claims, 2 Drawing Sheets

METHOD FOR MARKING OF A VESSEL AND A HANDLING DEVICE FOR APPLYING OF THE METHOD

This is a continuation of International Appln. No. PCT/FI94/00406 filed Sep. 15, 1994 which designated the U.S.

The object of the invention is a method to mark a container for the identification of the samples it contains, in which method the container is mounted in a holder, which has a memory unit for the storing of the machine readable identification data of the container in the holder. In addition, the object of the invention is the handling equipment for the application of the method, as defined in the introduction part of the first device claim.

The present known method for marking the samples is that bar code labels are glued to a test tube containing, for instance, blood samples. This label is printed by a printer when the person who took the sample types the identification code of the patient e.g., his name, into the patient data system.

The basic blood sample is transferred to the hospital laboratory where it is identified on the basis of the label glued to the test tube. After the patient who gave the sample is recognized by the bar code, the laboratory personnel is able to find out which tests should be done to the blood sample, on the basis of the record they have access to. On the basis of this, the basic blood sample is divided into partial samples by pipeting or by an automatic divider. A label is glued to the test tube of every partial sample and the necessary information needed for the identification of a patient is marked on the label either in plain text or by bar code.

The partial blood samples are brought to analyzers for the necessary tests. The results of these tests and the information on the labels are registered and forwarded to the doctor attending the patient.

The greatest drawback of the above mentioned known method is that the samples or the results of the samples may be mixed by human error making, naturally, the test results of the blood samples of the patients unreliable. This kind of an error may happen, for instance, in the process of dividing the basic blood, samples into partial samples in case the person doing the dividing accidentally glues a wrong label to a wrong test tube or in the registering of the results of the analysis. Also, there may be problems in the dividing of the sample into partial samples and/or in their handling. One particular problem is the inconvenience of handling the labels. The labels may come off or they are fastened so tight that their removal in the cleaning is difficult.

The purpose of this invention is to solve the above mentioned problems and to offer for use a very reliable and simple method and a handling equipment by which test tubes can be marked for identification, identified and handled so that there is no need for separate code labels and no risk of mixing the samples of different patients. In addition, the purpose of the invention is to introduce a method and a handling equipment by which the sample can be handled fast, reliably and in a predetermined way and by which all the necessary data to process the sample is following with the sample.

These goals are met by the method relating to the invention and by the handling equipment, which are characteristic of the claim 1 and of the first claim for equipment.

The invention is based on the idea that the identification data stored in the memory unit is read by the reading device of the handling equipment and the sample is handled, in a predetermined way, by the handling equipment instruments and the data necessary for the handling is transferred to the memory unit. The sample is identified positively and reliably by the handling equipment. Furthermore, the sample can be handled in a desired way, fast and securely, after the identification and the data needed for the processing and/or identification of the sample can be stored in the memory unit of the basic sample container or in the memory unit of further sample containers.

The method is extremely usable for the handling of the blood samples of the patients in a hospital. The container, in this application, refers to a test tube or equivalent usable for the handling of blood samples, urine samples etc. The handling refers to the procedures done to the sample in the container. This kind of a procedure is for example the dividing of the basic blood sample into partial samples for processing in various analyzers.

In the preferred application of the invention an inductively readable memory is used as a memory unit. Data, which is machine readable, can be stored in the memory unit, without having to turn the test tube to a certain position. Thus, all the data pertaining to the sample will be stored in the memory unit immediately after taking the sample. The advantage of this is also that the memory unit is reusable unlike the known bar code labels and it can be used repeatedly or even washed.

According to the method all the data necessary for the handling of the sample is stored in the memory unit of the holder. In practice, this is not possible when using bar code labels because the data that can be included in one bar code label is very limited. Because all the data necessary for the handling of the sample is readable from the memory of the holder, from where it can be transferred to the memory unit of the holder of the partial sample containers in the process of dividing the basic sample, the persons handling the sample do not need to use other information sources while handling the sample. The use of labels and equivalent marking divices is no more necessary. The marking of partial samples is easier because the handling equipment used in this method is a dividing device, because the dividing device automatically transferres the identification data from the memory unit of the holder of the basic blood sample into the memory unit of the holder of the respective partial blood sample. The most remarkable advantages of the method related to the invention are the minimizing of the chances of human error, the possibility of having simple and reliable information about what has to be done to the sample for example into how many partial samples it has to be divided and the possibility to find fast and simply, without the need of labels or equivalent devices, a specific sample among other similar ones just by reading the identification data in the memory unit of the holder.

In addition, the object of the invention is the handling equipment of the sample, characterized in that the handling equipment consists of a reading device for reading the identification data stored in the memory unit of the holder and of the instruments to handle the sample, identified by the identification data of the container, in a predetermined way. The most significant advantage of the handling equipment is that it automatically performs the predetermined measures to the sample like, for instance, divides it into partial samples after the handling equipment has identified the sample by the identification data stored in the memory unit of the holder. Thus, for instance, such a situation is avoided that a person handling a certain sample by mistake performs measures intended for another sample. Still, if he for instance does not divide the sample into sufficient number of portions, it is possible that there are not enough partial samples for all the analyzers needing partial samples.

In a preferred embodiment of the handling equipment according to the invention, the handling device is a dividing device for dividing the basic blood sample into partial samples, which dividing device is equipped with instruments to store the identification data it reads from the memory unit of the basic sample into the memory unit of each partial sample holder. Besides being simple, the most significant advantage of this method is the fact that the chance of human error is completely eliminated in the process of marking the sample for identification.

Figure 2:
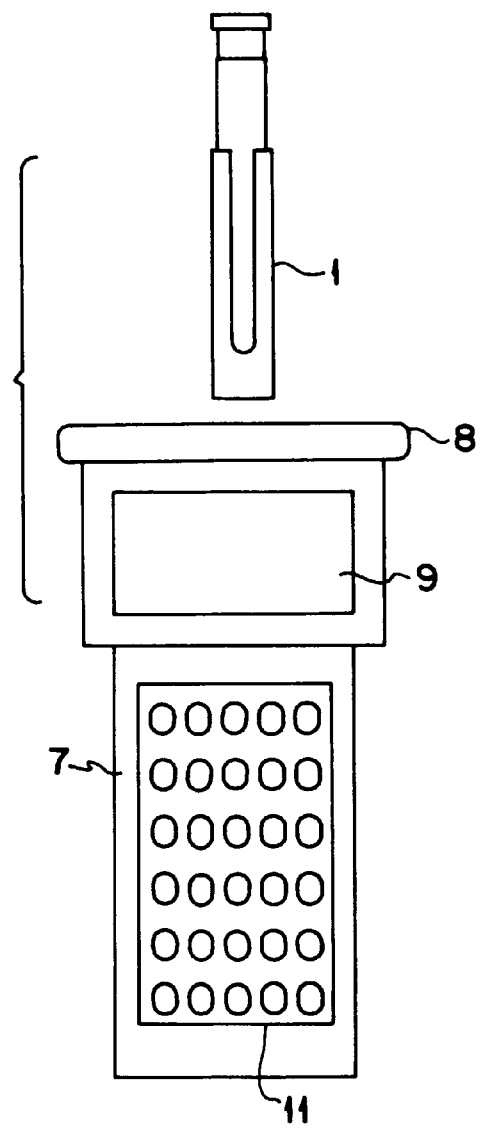
Figure 3:
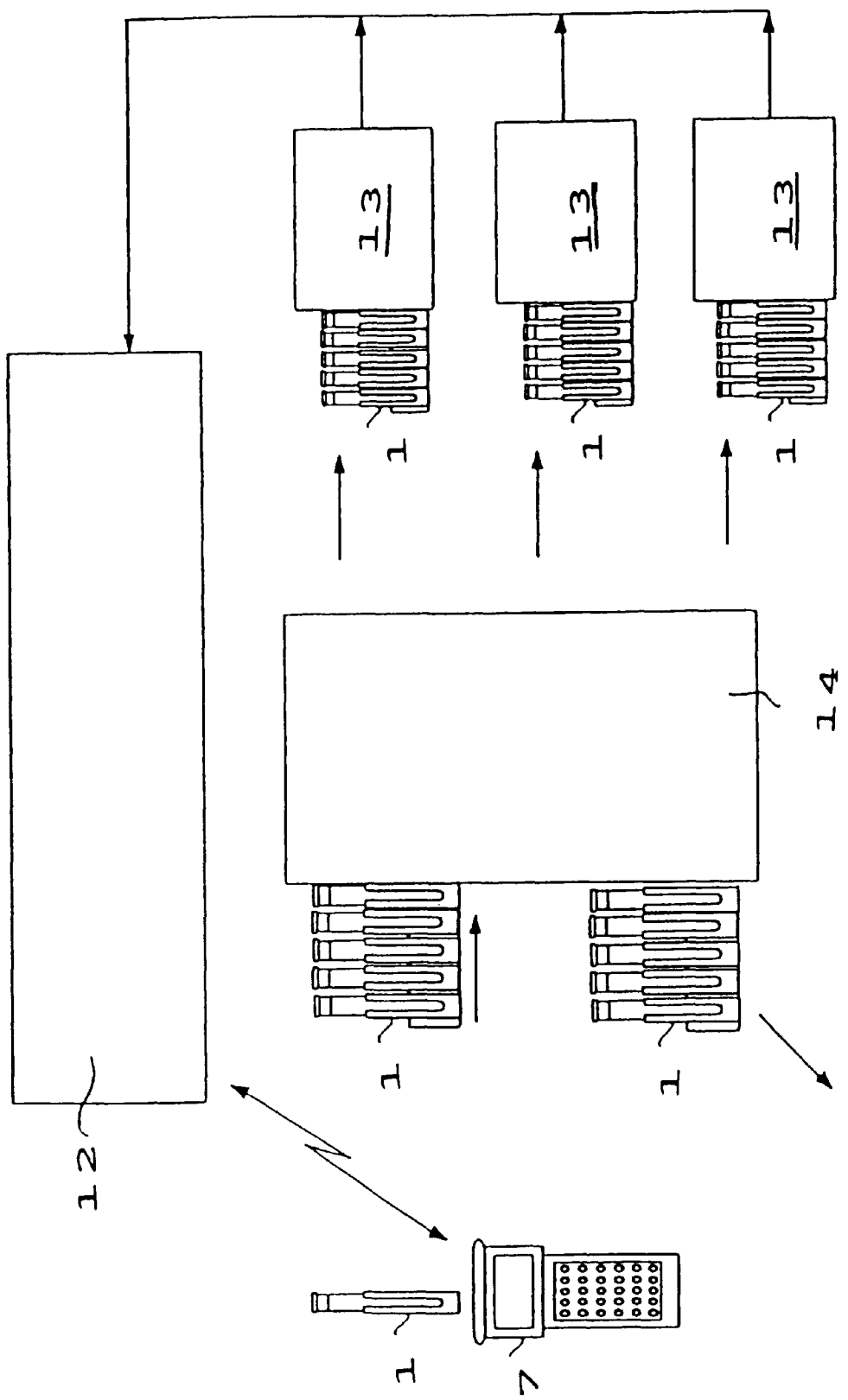

In the following, the invention is explained in greater detail with reference to the attached drawings, in which FIG. 1 shows a holder employed in the method, FIG. 2 shows a data terminal employed in the method of the invention, and FIG. 3 shows a preferred application of the equipment related to the method of the invention.

FIG. 1 shows the side view and partial cross-section of a holder 1. As illustrated in FIG. 1 a container 2, suitable for handling a blood sample or any other equivalent sample, is placed in a plastic holder 1. The container is a test tube which is properly closed by a plug 3. Both the holder 1 and the container 2 are of long cylindrical shape and round when viewed from above.

The diameter of the vertical cavity, open at the top, of the holder 1 is a bit smaller than the outside diameter of the holder 2. The walls of the holder 1 flex out by the pressure applied to them by the insertion of the container 2 into the vertical cavity of the holder. This flex-out is further helped by the vertical slot on the wall of the holder, which slot has the shape of the letter "U" as seen in FIG. 1. Besides helping the flex-out of the holder and the fastening of the container 2 into the holder 1, the slot makes it possible to see the filled amount inside the transparent container 2 even though the container is placed in the holder 1. The amount of fill may be estimated, depending on the situation, either by viewing or by automatic devices.

There is a cylindrical cavity underneath the bottom level of the vertical cavity of the holder 1. The memory unit 5 is attached into this cavity. The memory unit consists of a memory circuit, a sender, a receiver and a coil. The memory unit 5 is an inductively readable memory device the principle of which is described, for instance, in the FI-patent publication 85 079. Both the holder 1 and its memory unit are washable. The capacity of the memory circuit of the memory unit 5 is so designed that it can store the data of the patient who has given the blood sample in the container 2 and the data for the handling procedures of the blood sample in the container. Here the handling procedures refer to the analyses which have to be done to the blood sample. So the data in the memory circuits of the memory unit 5 is informative, for instance, as to who is the donor of the blood sample and the number of the analyses, in other words, into how many portions the blood sample in the container 2 has to be divided. All the data in the memory circuit is inductively readable which means that the data can be read without having to set the read head of the reading device in physical contact with the holder 1. There is no need to turn the holder into a certain position in relation to the read head, but the data can be read from the memory circuit just by bringing the memory circuit close to the read head of the reading device.

The bottom face of the holder 1 and the attached memory are perpendicular to the vertical centerline of the holder 1 and of the container 2, so the holder 1 stays in an upright position, as shown in FIG. 1, when it is put for instance on a table. Because of the holder 1, even the test tube 2 with a spherical bottom stays upright when placed in the holder 1.

FIG. 2 shows a portable data terminal 7, employed in a preferred application of the method of the invention. This data terminal can write and read data into and from the memory unit attached to the holder 1 in FIG. 1. The handheld terminal consists of the display 9 and the keyboard 11. To read or write data the holder 1 is brought close to the writing/reading head 8 of the terminal 7. Thus the data transfer between the memory unit of the holder and the terminal 7 is inductively performed. The advantageous wireless data transfer between the terminal 7 and the data system of the hospital enables the storing of the identification data for instance the names of those patients, who need to give a blood sample, into the terminal 7. After the blood sample is taken, the name of the patient is fed into the handheld terminal 7 through the keyboard and simultaneously the holder and the container holding the blood sample are brought close to the reading head of the handheld terminal. The data of the handling procedures of the blood sample is inductively transferred into the memory unit of the holder 1.

FIG. 3 shows a preferred embodiment of the equipment according to the invention. The blood samples of the patients and the tests to be done to the blood samples of each patient are fed into the hospital data system 12. Into the data system is also fed the data of all the analyzers 13 in the hospital, so the system is capable of deciding which analyzer or analyzers will perform the tests to the blood sample. The portable terminal 7 and the hospital data system have an advantageous wireless connection. This way the data of necessary blood samples can be transferred to the terminal 7. Accordingly, the nurse taking blood samples of the patients will have the information about who is to give a blood sample.

The blood sample is put in a container for example in the test tube 2 as shown in FIG. 1 and the test tube is placed in the holder 1 as shown in FIG. 1. The container holding the blood sample and the holder are brought close to the writing/reading head of the terminal 7 and by typing a code through the terminal keyboard the patient, who gave the sample, is identified. After the identification of the patient the data of the patient and the data concerning the tests that have to be done to the blood sample are transferred by the terminal to the memory unit attached to the holder 1.

After the blood samples have been taken, the containers holding the blood samples are transferred to the dividing device 14. The dividing device has a reading head for reading the data from the memory unit attached to the bottom of the holder 1. The reading head inductively reads the data from the memory unit. This data tells the following; who is the patient who gave the blood sample, into how many partial samples the blood sample in the container is to be divided and by which analyzers the tests to the blood sample are to be performed. On the basis of this information the blood sample in the container is divided into partial samples by the dividing device, and the partial samples are placed in containers to be transferred to various analyzers. The container, in which the basic blood sample has been, is transferred away from the dividing device to be washed and reused. The containers, into which the partial samples are placed, have memory units too and therefore while filling the partial sample containers, the dividing device inductively writes the identification data of the partial sample into the holder of each partial sample.

The filled containers of the partial samples are transferred to the analyzers 13, which perform the necessary analyses. During the process of analyzing the identification data of the patient is read from the holder of each respective partial sample for example the name of the patient. This particular identification data and the results of the performed analysis are fed into the hospital data system 12, where the doctor attending the patient can read it. In FIG. 3 the arrows starting from the right side of the analyzers 13 represent the data flow from the analyzers 13 into the hospital data system 12.

In another embodiment according to the invention only the data needed to identify the patient is stored in the memory of the holder 1 by the handheld terminal 7. In this particular application the dividing device 14 and the analyzers 13 are directly connected to the hospital data system 12 enabling them to receive other necessary information directly from the data system after the holder 1 has been identified by the identification data stored in its memory. For example, the dividing device 14 receives the information, concerning into how many portions the basic blood sample has to be divided, directly from the hospital data system 12. This is made possible by the identification data stored in the memory of the holder 1. Accordingly, the memory of the holder 1 can be minimized.

The above description and the related drawings must not be understood to limit the applications of the invention, but strictly illustrative. It shall be noticed that regardless of what has been said earlier about utilizing the invention in the handling of a blood sample, the invention can be utilized as well in the handling of any other sample like, for instance, in the handling of animal urine sample. Also, the reading and the writing of the memory do not necessarily need to be inductive, but any other similar technique can be applied. The method of the invention and the handling equipment can be varied within the scope of the annexed claims.

I claim:

1. A method for marking a container for identification, comprising:

placing a container in a holder, which includes a memory unit into which machine readable identification data of the container in the holder is stored;

reading the identification data stored in the memory unit by a reading device of a handling equipment;

processing a sample in the container by instruments of the handling equipment in a predetermined way;

during said processing dividing said sample and placing the resultant partial samples by the handling equipment from said container into one or several other containers having holders to which a memory unit is attached; and storing the identification data read from the memory of the holder of the basic sample in the first mentioned container by the handling equipment into the memory unit attached to the holders of each partial samples during the dividing.

2. A method as defined in claim 1, including using as said memory unit an inductively readable memory which includes a memory circuit, a sender, a receiver and a coil.

3. A method as defined in claim 1, wherein the sample in said first mentioned container is a blood sample and the method includes:

reading by the handling equipment from the memory unit of the holder of the basic sample the number of the necessary partial samples.

* * * * *